United States Patent [19]
Hillman et al.

[11] Patent Number: 5,792,626
[45] Date of Patent: Aug. 11, 1998

[54] HUMAN INTERFERON-INDUCIBLE PROTEIN

[75] Inventors: Jennifer L. Hillman, San Jose; Phillip R. Hawkins, Mountain View, both of Calif.

[73] Assignee: Incyte Pharmaceuticals, Inc., Palo Alto, Calif.

[21] Appl. No.: 716,588

[22] Filed: Sep. 18, 1996

[51] Int. Cl.$^6$ .............................. C07K 1/00; A01K 37/18; C07H 21/02; C07H 21/04

[52] U.S. Cl. ............................ 435/69.1; 514/2; 536/23.1; 536/24.3; 536/25.3; 435/70.1; 435/172.1; 530/350

[58] Field of Search ............................ 536/23.1, 24.3, 536/25.3; 435/172.1, 69.1, 70.1; 530/350; 514/2

[56] References Cited

PUBLICATIONS

Hardman, J.G., et al., "The Pharmacological Basis of Therapeutics", pp. 1211–1215 (1996).

Kato, T., et al., "Interferon–Inducible Gene Expression in Chimpanzee Livber Infected with Hepatitis C Virus", *Virology*, 190:856–860 (1992).

Kelly, J.M., et al., "Characterization of a human gene inducible by α–and β–interferons and its expression in mouse cells", *EMBO J*, 5:1601–1606 (1986).

Rasmussen, U.B., et al., "Indentification of a New Interferon–α–inducible Gene (p27) on Human Chromosome 14q32 and Its Expression in Breast Carcinoma", *Cancer Res.*, 53:4096–4101 (1993).

*Primary Examiner*—Lila Feisee
*Assistant Examiner*—Ray F. Ebert
*Attorney, Agent, or Firm*—Lucy J. Billings

[57] ABSTRACT

The present invention provides a novel human interferon-inducible protein (HIFI) and the polynucleotides which identify and encode HIFI. The invention provides for genetically engineered expression vectors and host cells comprising the nucleic acid sequence encoding HIFI and for a method for producing the protein. The invention also provides compositions containing HIFI.

8 Claims, 4 Drawing Sheets

```
                9              18             27              36             45              54
5' TCT TAC CAC GCG TCG CCC CGA TTA TGG GGC CTC GCG GAC CGC ACC AGT GCC GGC 63             72             81              90             99             108
   GGG AGA GCT GGC TTG GGG CGC TGG CAC CTC CTC TTA CAG CTT TAC TCC TGC CAG 117            126            135             144            153             162
   CTT GGG AAA AGG CCG GAG AAG GTG AAA TTC TGT GTG CTC CCT CCG GCG AGA GAC 171            180            189             198            207             216
   TTT GTC AGC TCC CGC ACA GTA ACA TCC TGA ATA AAG TCA AAA CTC AAC CAA CAG 225            234            243             252            261             270
   GTG GAA GTC CAA GAA TCC GAG TGG AGG CTC ACC GAG GCG AAG GGG CCA ACC ATG
                                                                             M 279            288            297             306            315             324
   GGA AAG GAG AGT GGA TGG GAC TCA GGC AGG GCT GCT GTA GCA GCT GTG GTC GGA
   G   K   E   S   G   W   D   S   G   R   A   A   V   A   A   V   V   G 333            342            351             360            369             378
   GGA GTT GTG GCT GTG GGG ACT GTG CTC GTG GCG CTC AGT GCC ATG GGC TTC ACC
   G   V   V   A   V   G   T   V   L   V   A   L   S   A   M   G   F   T 387            396            405             414            423             432
   TCA GTA GGA ATC GCC GCA TCC TCC ATA GCA GCC AAG ATG ATG TCT ACA GCA GCC
   S   V   G   I   A   A   S   S   I   A   A   K   M   M   S   T   ?   A 441            450            459             468            477             486
   ATT GCC AAC GGG GGC GGA GTT GCT GCT GGC AGT CTG GTG GCT ATT CTG CAG TCA
   I   A   N   G   G   G   V   A   A   G   S   L   V   A   I   L   Q   S 495            504            513             522            531             540
   GTG GGG GCA GCT GGA CTC TCT GTG ACA TCT AAA GTT ATC GGG GGC TTT GCT GGG
   V   G   A   A   G   L   S   V   T   S   K   V   I   G   G   F   A   G 549            558            567             576            585             594
   ACA NCT CTT GGG GCC TGG CTG GGT TCA NCC CCT TCC AGC TGA ACA NCA CAC TGA
   T   X   L   G   A   W   L   G   S   X   P   S   S   *

603            612            621             630            639             648
   GGC AGG GAG TTG GCT CTC TTG GTG GAG ATG ACT TTC CTG GGC CTC TGG ATG ACA 657            666            675             684
   ATC TTC CAA AGG ACA AGT CTN CTA CTT CCA AAA CTA GG 3'
```

FIGURE 1

```
1    M G K E S G W D - - - - - - - - - S G R A A V A - - - - -                HIFI
1    M E A S A L T S - - - - - - - - - S A V T S V A K V V R V                GI 35184
1    M R Q K A V S V F L C Y L L L F T C S G V E A G K K K C S E              GI 32698
1    M R Q K A V S L F L C Y L L L F T C S G V E A G K K K C S E              GI 218574

16   - - - - - - - - - - - - - - - - - A V V G G V V A V G T V L V A          HIFI
21   A S G S A V V L P L A R I A T V V I G G V V A M A A V P M V              GI 35184
31   S S D S G S G F - W K A L T F M A V G G G L A V A G - - - -              GI 32698
31   S S D S G S G F - W K A L T F M A V G G G L A V A G - - - -              GI 218574

31   L S A M G F T S V G I A A S S I A A K M M S T A A I A N G G              HIFI
51   L S A M G F T A A G I A S S S I A A K M M S A A A I A N G G              GI 35184
56   L P A L G F T G A G I A A N S V A A S L M S W S A I L N G G              GI 32698
56   L P A L G F T G A G I A A N S V A A S L M S W S A I L N G G              GI 218574

61   G V A A G S L V A I L Q S V G A A G L S V T S K V I G G F A              HIFI
81   G V A S G S L V G T L Q S L G A T G L S G L T K F I L G S I              GI 35184
86   G V P A G G L V A T L Q S L G A G G S V V I G N I G A L M                GI 32698
86   G V P A G G L V A T L Q S L G A G G S V I T G N I G A L M                GI 218574

91   G T X L G A W L G S X P S S                                              HIFI
111  G S A I A A V I A R F - - Y                                              GI 35184
116  R Y A T H K Y L D S E E D E E                                            GI 32698
116  G Y A T H K Y L D S E E D E E                                            GI 218574
```

FIGURE 2

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:

( A ) LENGTH: 104 amino acids
( B ) TYPE: amino acid
( C ) STRANDEDNESS: single
( D ) TOPOLOGY: linear ( i i ) MOLECULE TYPE: peptide ( v i i ) IMMEDIATE SOURCE:
( A ) LIBRARY: KIDNNOT05
( B ) CLONE: 628430

( x i ) SEQUENCE DESCRIPTION: SEQ ID NO:1:

```
Met Gly Lys Glu Ser Gly Trp Asp Ser Gly Arg Ala Ala Val Ala Ala
  1               5                  10                  15

Val Val Gly Gly Val Val Ala Val Gly Thr Val Leu Val Ala Leu Ser
             20                  25                  30

Ala Met Gly Phe Thr Ser Val Gly Ile Ala Ala Ser Ser Ile Ala Ala
         35                  40                  45

Lys Met Met Ser Thr Ala Ala Ile Ala Asn Gly Gly Gly Val Ala Ala
     50                  55                  60

Gly Ser Leu Val Ala Ile Leu Gln Ser Val Gly Ala Ala Gly Leu Ser
65                   70                  75                  80

Val Thr Ser Lys Val Ile Gly Gly Phe Ala Gly Thr Xaa Leu Gly Ala
             85                  90                  95

Trp Leu Gly Ser Xaa Pro Ser Ser
            100
```

( 2 ) INFORMATION FOR SEQ ID NO:2:

( i ) SEQUENCE CHARACTERISTICS:
( A ) LENGTH: 686 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( A ) LIBRARY: KIDNNOT05
( B ) CLONE: 628430

( x i ) SEQUENCE DESCRIPTION: SEQ ID NO:2:

```
TCTTACCACG CGTCGCCCCG ATTATGGGGC CTCGCGGACC GCACCAGTGC CGGCGGGAGA      60
GCTGGCTTGG GGCGCTGGCA CCTCCTCTTA CAGCTTTACT CCTGCCAGCT TGGGAAAAGG     120
CCGGAGAAGG TGAAATTCTG TGTGCTCCCT CCGGCGAGAG ACTTTGTCAG CTCCCGCACA    180
GTAACATCCT GAATAAAGTC AAAACTCAAC CAACAGGTGG AAGTCCAAGA ATCCGAGTGG    240
AGGCTCACCG AGGCGAAGGG GCCAACCATG GGAAAGGAGA GTGGATGGGA CTCAGGCAGG    300
GCTGCTGTAG CAGCTGTGGT CGGAGGAGTT GTGGCTGTGG GGACTGTGCT CGTGGCGCTC    360
AGTGCCATGG GCTTCACCTC AGTAGGAATC GCCGCATCCT CCATAGCAGC CAAGATGATG    420
TCTACAGCAG CCATTGCCAA CGGGGGCGGA GTTGCTGCTG GCAGTCTGGT GGCTATTCTG    480
CAGTCAGTGG GGCAGCTGG  ACTCTCTGTG ACATCTAAAG TTATCGGGG  CTTTGCTGGG    540
ACANCTCTTG GGGCCTGGCT GGGTTCANCC CCTTCCAGCT GAACANCACA CTGAGGCAGG    600
GAGTTGGCTC TCTTGGTGGA GATGACTTTC CTGGGCCTCT GGATGACAAT CTTCCAAAGG    660
ACAAGTCTNC TACTTCCAAA ACTAGG                                         686
```

( 2 ) INFORMATION FOR SEQ ID NO:3:

( i ) SEQUENCE CHARACTERISTICS:
( A ) LENGTH: 122 amino acids ( B ) TYPE: amino acid
( C ) STRANDEDNESS: single
( D ) TOPOLOGY: linear ( i i ) MOLECULE TYPE: peptide ( v i i ) IMMEDIATE SOURCE:
( A ) LIBRARY: GenBank
( B ) CLONE: 35184

( x i ) SEQUENCE DESCRIPTION: SEQ ID NO:3:

```
Met Glu Ala Ser Ala Leu Thr Ser Ser Ala Val Thr Ser Val Ala Lys
 1               5                  10                  15
Val Val Arg Val Ala Ser Gly Ser Ala Val Val Leu Pro Leu Ala Arg
            20                  25                  30
Ile Ala Thr Val Val Ile Gly Gly Val Val Ala Met Ala Ala Val Pro
        35                  40                  45
Met Val Leu Ser Ala Met Gly Phe Thr Ala Ala Gly Ile Ala Ser Ser
    50                  55                  60
Ser Ile Ala Ala Lys Met Met Ser Ala Ala Ala Ile Ala Asn Gly Gly
65                  70                  75                  80
Gly Val Ala Ser Gly Ser Leu Val Gly Thr Leu Gln Ser Leu Gly Ala
                85                  90                  95
Thr Gly Leu Ser Gly Leu Thr Lys Phe Ile Leu Gly Ser Ile Gly Ser
                100                 105                 110
Ala Ile Ala Ala Val Ile Ala Arg Phe Tyr
                115                 120
```

( 2 ) INFORMATION FOR SEQ ID NO:4:

( i ) SEQUENCE CHARACTERISTICS:
( A ) LENGTH: 130 amino acids
( B ) TYPE: amino acid
( C ) STRANDEDNESS: single
( D ) TOPOLOGY: linear ( i i ) MOLECULE TYPE: peptide ( v i i ) IMMEDIATE SOURCE:
( A ) LIBRARY: GenBank
( B ) CLONE: 32698

( x i ) SEQUENCE DESCRIPTION: SEQ ID NO:4:

```
Met Arg Gln Lys Ala Val Ser Val Phe Leu Cys Tyr Leu Leu Leu Phe
 1               5                  10                  15
Thr Cys Ser Gly Val Glu Ala Gly Lys Lys Lys Cys Ser Glu Ser Ser
            20                  25                  30
Asp Ser Gly Ser Gly Phe Trp Lys Ala Leu Thr Phe Met Ala Val Gly
        35                  40                  45
Gly Gly Leu Ala Val Ala Gly Leu Pro Ala Leu Gly Phe Thr Gly Ala
    50                  55                  60
Gly Ile Ala Ala Asn Ser Val Ala Ala Ser Leu Met Ser Trp Ser Ala
65                  70                  75                  80
Ile Leu Asn Gly Gly Gly Val Pro Ala Gly Gly Leu Val Ala Thr Leu
                85                  90                  95
Gln Ser Leu Gly Ala Gly Gly Ser Ser Val Val Ile Gly Asn Ile Gly
                100                 105                 110
Ala Leu Met Arg Tyr Ala Thr His Lys Tyr Leu Asp Ser Glu Glu Asp
                115                 120                 125
Glu Glu
    130
```

( 2 ) INFORMATION FOR SEQ ID NO:5:

( i ) SEQUENCE CHARACTERISTICS:
        ( A ) LENGTH: 130 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 218574

( x i ) SEQUENCE DESCRIPTION: SEQ ID NO:5:

```
Met Arg Gln Lys Ala Val Ser Leu Phe Leu Cys Tyr Leu Leu Leu Phe
 1               5                  10                  15
Thr Cys Ser Gly Val Glu Ala Gly Lys Lys Lys Cys Ser Glu Ser Ser
            20                  25                  30
Asp Ser Gly Ser Gly Phe Trp Lys Ala Leu Thr Phe Met Ala Val Gly
            35                  40                  45
Gly Gly Leu Ala Val Ala Gly Leu Pro Ala Leu Gly Phe Thr Gly Ala
    50                  55                  60
Gly Ile Ala Ala Asn Ser Val Ala Ala Ser Leu Met Ser Trp Ser Ala
65                  70                  75                  80
Ile Leu Asn Gly Gly Gly Val Pro Ala Gly Gly Leu Val Ala Thr Leu
                85                  90                  95
Gln Ser Leu Gly Ala Gly Gly Ser Ser Val Ile Thr Gly Asn Ile Gly
            100                 105                 110
Ala Leu Met Gly Tyr Ala Thr His Lys Tyr Leu Asp Ser Glu Glu Asp
            115                 120                 125
Glu Glu
130
```

HUMAN INTERFERON-INDUCIBLE PROTEIN

FIELD OF THE INVENTION

The present invention relates to nucleic acid and amino acid sequences of a novel human interferon-inducible protein and to the use of these sequences in the diagnosis, study, prevention and treatment of disease.

BACKGROUND OF THE INVENTION

Interferons (IFNs) are a part of the group of intercellular messenger proteins known as cytokines. α-IFN is the product of a multigene family of at least 16 members, whereas β-IFN is the product of a single gene. α- and β-IFNs are also known as type I IFNs. Type I IFNs are produced in a variety of cells types. Biosynthesis of type I IFNs is stimulated by viruses and other pathogens, and by various cytokines and growth factors. γ-IFN, also known as type II IFN, is produced in T-cells and natural killer cells. Biosynthesis of type II IFN is stimulated by antigens to which the organism has been sensitized. Both α- and γ-IFNs are immunomodulators and anti-inflammatory agents, activating macrophages, T-cells and natural killer cells.

IFNs are part of the body's natural defense to viruses and tumors. They exert these defenses by affecting the function of the immune system and by direct action on pathogens and tumor cells. IFNs mediate these multiple effects in part by inducing the synthesis of many cellular proteins. Some interferon-inducible (IFI) genes are induced equally well by α-, β- and γ-IFNs. Other IFI genes are preferentially induced by the type I or by the type II IFNs.

The various proteins produced by IFI genes possess antitumor, antiviral and immunomodulatory functions. The expression of tumor antigens in cancer cells is increased by α-IFN, and renders the cancer cells more susceptible to immune rejection. The IFI proteins synthesized in response to viral infections are known to inhibit viral functions such as cell penetration, uncoating, RNA and protein synthesis, assembly and release (cf Hardman J. G. et al (1996) *The Pharmacological Basis of Therapeutics*, McGraw-Hill, New York, N.Y. pp 1211–1214). Type II IFN stimulates expression of major histocompatibility complex (MHC) proteins and is thus used in immune response enhancement.

An IFI gene known as 6-16 encodes an mRNA which is highly induced by type I IFNs in a variety of human cells (Kelly J. M. et al (1986) EMBO J 5:1601–1606). After induction, 6-16 mRNA constitutes as much as 0.1% of the total cellular mRNA. The 6-16 mRNA is present at only very low levels in the absence of type I IFN, and is only weakly induced by type II IFN.

The 6-16 mRNA encodes a hydrophobic protein of 130 amino acids. The first 20 to 23 amino acids comprise a putative signal peptide. Protein 6-16 has at least two predicted transmembrane regions culminating in a negatively charged C-terminus.

The p27 gene encodes a protein with 41% amino acid sequence identity to the 6-16 protein. The p27 gene is expressed in some breast tumor cell lines and in a gastric cancer cell line. In other breast tumor cell lines, in the HeLa cervical cancer cell line, and in fetal lung fibroblasts, p27 expression occurs only upon α-IFN induction. In one breast tumor cell line, p27 is independently induced by estradiol and by IFN (Rasmussen U. B. et al (1993) Cancer Res 53:4096–4101).

Expression of p27 was analyzed in 21 primary invasive breast carcinomas, 1 breast cancer bone metastasis, and 3 breast fibroadenomas. High levels of p27 were found in about one-half of the primary carcinomas and in the bone metastasis, but not in the fibroadenomas. These observations suggest that certain breast tumors may produce high levels of, or have increased sensitivity to, type I IFN as compared to other breast tumors (Rasmussen U. B. et al, supra). In addition, the p27 gene is expressed at significant levels in normal tissues including colon, stomach and lung, but not expressed in placenta, kidney, liver or skin. (Rasmussen UB et al, supra).

The small hydrophobic IFI gene products may contribute to viral resistance. A hepatitis-C virus (HCV)-induced gene, 130-51, was isolated from a cDNA library prepared from chimpanzee liver during the acute phase of the infection. The protein product of this gene has 97% identity to the human 6-16 protein (Kato T. et al (1992) Virology 190:856–860). The investigators suggest that HCV infection actively induces IFN expression, which in turn induces expression of IFI genes including 130-51.

The IFI proteins synthesized in response to viral infections are known to inhibit viral functions such as penetration, uncoating, RNA or protein synthesis, assembly or release. The 130-51 protein may inhibit one or more of these functions in HCV. A particular virus may be inhibited in multiple functions by IFI proteins. In addition, the principle inhibitory effect exerted by IFI proteins differs among the virus families (Hardman J. G., supra, p 1211).

The hydrophobic IFI proteins of the invention may provide the basis for clinical diagnosis of diseases associated with their induction. These proteins may be useful in the diagnosis and treatment of tumors, viral infections, inflammation, or conditions associated with impaired immunity. Furthermore, these proteins may be used for investigations of the control of gene expression by IFNs and other cytokines in normal and diseased cells.

SUMMARY OF THE INVENTION

The present invention features a novel small hydrophobic IFI protein, hereinafter referred to as HIFI, having chemical and structural homology to human IFI protein isoforms p27 and 6-16, and the chimpanzee homolog 130-51. Accordingly, the invention features a substantially purified HIFI, having the amino acid sequence of SEQ ID NO:1, and the structural characteristics of the family of small hydrophobic IFI proteins.

One aspect of the invention features isolated and substantially purified polynucleotides which encode HIFI. In a particular aspect, the polynucleotide is the nucleotide sequence of SEQ ID NO:2. In addition, the invention features nucleotide sequences which hybridize under stringent conditions to SEQ ID NO:2.

The invention further relates to nucleic acid sequence encoding HIFI, oligonucleotides, peptide nucleic acids (PNA), fragments, portions or antisense molecules thereof. The present invention also relates to an expression vector which includes polynucleotide encoding HIFI, its use to transform host cells or organisms and methods for producing the protein. The invention also relates to antibodies which bind specifically to HIFI and to a pharmaceutical composition comprising substantially purified HIFI.

BRIEF DESCRIPTION OF THE FIGURES

FIG. 1 show the amino acid sequence (SEQ ID NO:1) and the nucleic acid sequence (SEQ ID NO:2) of the human IFI protein HIFI. The alignment was produced using MacDNAsis software (Hitachi Software Engineering Co Ltd, San Bruno, Calif.).

FIG. 2 shows the amino acid sequence alignments among HIFI (SEQ ID NO:1), human proteins p27 (GI 35184; SEQ ID NO:3) and 6-16 (GI 32698; SEQ ID NO:4), and chimpanzee protein 130-51 (GI 218574, SEQ ID NO:5). The multisequence alignment program of DNAStar software (DNAStar Inc. Madison, Wisc.) was used.

DETAILED DESCRIPTION OF THE INVENTION

Definitions

Figure 3:
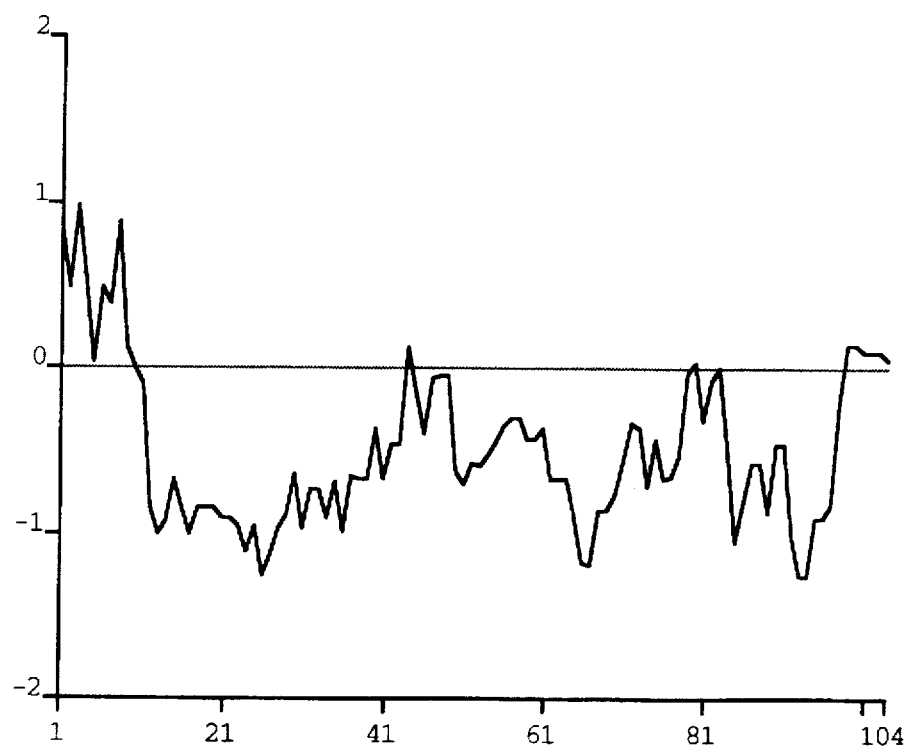
FIG. 3 shows the hydrophobicity plot (generated using MacDNAsis software) for HIFI, SEQ ID NO:1; the X axis reflects amino acid position, and the negative Y axis, hydrophobicity.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Consensus" as used herein may refer to a nucleic acid sequence 1) which has been resequenced to resolve uncalled bases, 2) which has been extended using XL-PCR (Perkin Elmer) in the 5' or the 3' direction and resequenced, 3) which has been assembled from the overlapping sequences of more than one Incyte clone GCG Fragment Assembly System, (GCG, Madison, Wisc.), or 4) which has been both extended and assembled.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen PE et al (1993) Anticancer Drug Des 8:53–63).

A "variant" of HIFI is defined as an amino acid sequence that is different by one or more amino acid substitutions. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring HIFI.

A "substitution" results from the replacement of one or more nucleotides or amino acids by different nucleotides or amino acids, respectively.

The term "biologically active" refers to a HIFI having structural, regulatory or biochemical functions of the naturally occurring HIFI. Likewise, "immunologically active" defines the capability of the natural, recombinant or synthetic HIFI, or any oligopeptide thereof, to induce a specific immune response in appropriate animals or cells and to bind with specific antibodies.

The term "derivative" as used herein refers to the chemical modification of a nucleic acid encoding HIFI or the encoded HIFI. Illustrative of such modifications would be replacement of hydrogen by an alkyl, acyl, or amino group. A nucleic acid derivative would encode a polypeptide which retains essential biological characteristics of natural HIFI.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm-5° C. (5° C. below the Tm of the probe) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J. (1994) *Dictionary of Biotechnology*, Stockton Press, New York, N.Y.). Amplification as carried out in the polymerase chain reaction technologies is described in Dieffenbach C. W. and G. S. Dveksler (1995, *PCR Primer, a Laboratory Manual*, Cold Spring Harbor Press, Plainview, N.Y.).

Preferred Embodiments

The present invention relates to a novel human IFI protein (HIFI) identified among the cDNAs from a library constructed from human neonatal kidney (KIDNNOT05) and to the use of the nucleic acid and amino acid sequences disclosed herein in the study, diagnosis, prevention and treatment of disease. The nucleotide sequence disclosed herein was extended using XL-PCR (Perkin-Elmer, Norwalk, Conn.) and Incyte Clone 628430. Northern analysis using the LIFESEQ™ database (Incyte Pharmaceuticals, Palo Alto, Calif.) shows that mRNA encoding HIFI was found only in neonatal kidney. It must be noted that naturally occurring expression of HIFI is not necessarily limited to this tissue.

The present invention also encompasses HIFI variants. A preferred HIFI variant is one having at least 80% amino acid sequence similarity to the amino acid sequence (SEQ ID NO:1), a more preferred HIFI variant is one having at least 90% amino acid sequence similarity to SEQ ID NO:1 and a most preferred HIFI variant is one having at least 95% amino acid sequence similarity to SEQ ID NO:1.

The nucleic acid sequence encoding the HIFI of the present invention was first identified in the cDNA, Incyte Clone 628430, through a computer-generated search for amino acid sequence alignments. The nucleic acid sequence, SEQ ID NO:2, disclosed herein (FIG. 1) encodes the amino acid sequence, SEQ ID NO:1, designated HIFI.

The present invention is based in part on the structural homology shown in FIG. 2, among HIFI and other small hydrophobic IFI proteins including p27 (GI 35184; Rasmussen et al, supra) and 6-16 (GI 32698, Kelly et al, supra) from human and 130-51 from chimpanzee (GI 218574, Kato et al, supra). P27, 6-16, and 130-51 have, respectively, 55%, 45% and 46% amino acid sequence identity to HIFI.

Figure 4:
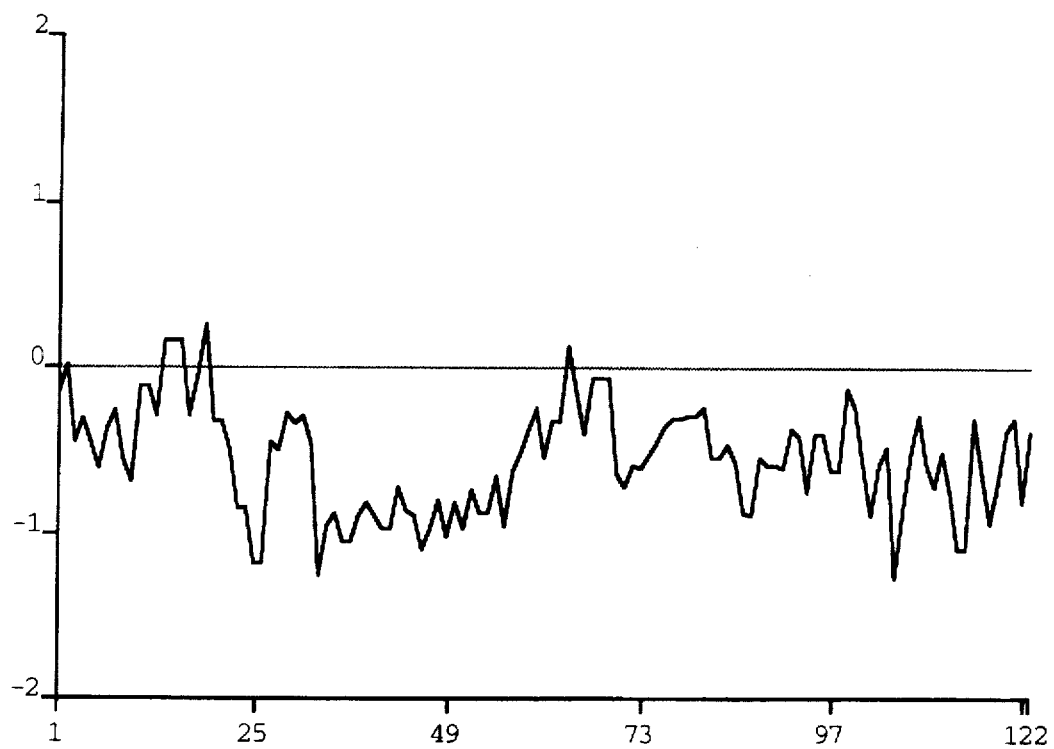
FIG. 4 shows the hydrophobicity plot (generated using MacDNAsis software) for p27, SEQ ID NO:3; the X axis reflects amino acid position, and the negative Y axis, hydrophobicity.

The HIFI protein sequence consists of 104 amino acids. From the amino acid sequence alignments (FIG. 2) and the hydrophobicity plots of HIFI and p27 (FIGS. 3 and 4), HIFI has three predicted transmembrane domains spanning residues 16-36, 51-71 and 79-99. HIFI contains no cysteines and no potential N-glycosylation sites.

The HIFI Coding Sequences

The extended nucleic acid and deduced amino acid sequences of HIFI are shown in FIG. 1. In accordance with the invention, any nucleic acid sequence which encodes the amino acid sequence of HIFI can be used to generate recombinant molecules which express HIFI. In a specific embodiment described herein, a partial sequence encoding HIFI was first isolated as Incyte Clone 628430 from a human neonatal kidney library (KIDNNOT05).

It will be appreciated by those skilled in the art that as a result of the degeneracy of the genetic code, a multitude of nucleotide sequences encoding HIFI, some bearing minimal homology to the nucleotide sequences of any known and naturally occurring gene, may be produced. The invention contemplates each and every possible variation of nucleotide sequence that could be made by selecting combinations based on possible codon choices. These combinations are made in accordance with the standard triplet genetic code as applied to the nucleotide sequence of naturally occurring HIFI, and all such variations are to be considered as being specifically disclosed.

Although nucleotide sequences which encode HIFI and its variants are preferably capable of hybridizing to the nucleotide sequence of the naturally occurring HIFI under appropriately selected conditions of stringency, it may be advantageous to produce nucleotide sequences encoding HIFI or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HIFI and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a HIFI and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a gene encoding HIFI.

Also included within the scope of the present invention are polynucleotide sequences that are capable of hybridizing to the nucleotide sequence of FIG. 1 under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego, Calif.) incorporated herein by reference, and confer may be used at a defined stringency.

Altered nucleic acid sequences encoding HIFI which may be used in accordance with the invention include deletions, insertions or substitutions of different nucleotides resulting in a polynucleotide that encodes the same or a functionally equivalent HIFI. The protein may also show deletions, insertions or substitutions of amino acid residues which produce a silent change and result in a functionally equivalent HIFI. Deliberate amino acid substitutions may be made on the basis of similarity in polarity, charge, solubility, hydrophobicity, hydrophilicity, and/or the amphipathic nature of the residues as long as the biological activity of HIFI is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of HIFI. As used herein, an "allele" or "allelic sequence" is an alternative form of HIFI. Alleles result from a mutation, ie. a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (US Biochemical Corp, Cleveland, Ohio), Taq polymerase (Perkin Elmer, Norwalk Conn.), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; M. J. Research, Watertown, Mass.) and the ABI 377 DNA sequencers (Perkin Elmer).

Extending the Polynucleotide Sequence

The polynucleotide sequence encoding HIFI may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T. et al (1988) Nucleic Acids Res 16:8186). The primers may be designed using OLIGO® 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker J. D. et al (1991; Nucleic Acids Res 19:3055–60). Additionally, one can use PCR, nested primers and PromoterFinder libraries to walk in genomic DNA (PromoterFinder1 Clontech (Palo Alto, Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton, Calif.), and other companies. Capillary sequencing may employ flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M. C. et al (1993) Anal Chem 65:2851–8).

Expression of the Nucleotide Sequence

In accordance with the present invention, polynucleotide sequences which encode HIFI, fragments of the polypeptide, fusion proteins or functional equivalents thereof may be used in recombinant DNA molecules that direct the expression of HIFI in appropriate host cells. Due to the inherent degeneracy of the genetic code, other DNA sequences which encode substantially the same or a functionally equivalent amino acid sequence, may be used to clone and express HIFI. As will be understood by those of skill in the art, it may be advantageous to produce HIFI-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of HIFI expression or to produce recombinant RNA transcripts having desirable properties, such as a longer half-life, than transcripts produced from naturally occurring sequence.

The nucleotide sequences of the present invention can be engineered in order to alter a coding sequence of HIFI for a variety of reasons, including but not limited to, alterations which modify the cloning, processing and/or expression of the gene product. For example, mutations may be introduced using techniques which are well known in the art, eg. site-directed mutagenesis to insert new restriction sites, to alter glycosylation patterns, to change codon preference, to produce splice variants, etc.

In another embodiment of the invention, a natural, modified or recombinant nucleotide sequence encoding HIFI may be ligated to a heterologous sequence to encode a fusion protein. For example, for screening of peptide libraries for inhibitors of HIFI activity, it may be useful to encode a chimeric HIFI protein that is recognized by a commercially available antibody. A fusion protein may also be engineered to contain a cleavage site located between a HIFI sequence and the heterologous protein sequence, so that the HIFI may be cleaved and substantially purified away from the heterologous moiety.

In an alternate embodiment of the invention, the coding sequence for HIFI may be synthesized, whole or in part, using chemical methods well known in the art (see Caruthers M. H. et al (1980) Nuc Acids Res Symp Ser 215–23, Horn T et al(1980) Nuc Acids Res Symp Ser 225–32, etc). Alternatively, the protein itself could be produced using chemical methods to synthesize a HIFI amino acid sequence, whole or in part. For example, peptide synthesis can be performed using various solid-phase techniques (Roberge J. Y. et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg. Creighton (1983) *Proteins, Structures and Molecular Principles*, W. H. Freeman and Co, New York, N.Y.). The composition of the synthetic peptides may be confirmed by amino acid analysis or sequencing (eg. the Edman degradation procedure; Creighton, supra). Additionally the amino acid sequence of HIFI, or any part thereof, may be altered during direct synthesis and/or combined using chemical methods with sequences from other proteins, or any part thereof, to produce a variant polypeptide.

Expression Systems

In order to express a biologically active HIFI, the nucleotide sequence encoding HIFI or its functional equivalent, is inserted into an appropriate expression vector, ie. a vector which contains the necessary elements for the transcription and translation of the inserted coding sequence.

Methods which are well known to those skilled in the art can be used to construct expression vectors containing a HIFI coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview, N.Y. and Ausubel F. M. et al (1989) *Current Protocols in Molecular Biology*, John Wiley & Sons, New York, N.Y.

A variety of expression vector/host systems may be utilized to contain and express a HIFI coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg. baculovirus); plant cell systems transfected with virus expression vectors (eg. cauliflower mosaic virus, CaMV; tobacco mosaic virus, TMV) or transformed with bacterial expression vectors (eg. Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of HIFI, vectors based on SV40 or EBV may be used with an appropriate selectable marker.

In bacterial systems, a number of expression vectors may be selected depending upon the use intended for HIFI. For example, when large quantities of HIFI are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the HIFI coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison, Wisc.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding HIFI may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J. and Sinibaldi R. M. (1991) Results Probl Cell Differ 17:85–105) may be used. These constructs can be introduced into plant cells by direct DNA transformation or pathogen-mediated transfection. For reviews of such techniques, see Hobbs S. or Murry L. E. in McGraw Hill *Yearbook of Science and Technology* (1992) McGraw Hill New York, N.Y., pp 191–196 or Weissbach and Weissbach (1988) *Methods for Plant Molecular Biology*, Academic Press, New York, N.Y., pp 421–463.

An alternative expression system which could be used to express HIFI is an insect system. In one such system, *Autographa californica* nuclear polyhedrosis virus (AcNPV) is used as a vector to express foreign genes in *Spodooptera frugiperda* cells or in Trichoolusia larvae. The HIFI coding sequence may be cloned into a nonessential region of the virus, such as the polyhedrin gene, and placed under control of the polyhedrin promoter. Successful insertion of the HIFI coding sequence will render the polyhedrin gene inactive and produce recombinant virus lacking coat protein coat. The recombinant viruses are then used to infect *S. frugicerda* cells or Trichoplusia larvae in which HIFI is expressed (Smith et al (1983) J Virol 46:584; Engelhard E. K. et al (1994) Proc Nat Acad Sci 91:3224–7).

In mammalian host cells, a number of viral-based expression systems may be utilized. In cases where an adenovirus is used as an expression vector, a coding sequence for HIFI may be ligated into an adenovirus transcription/translation complex consisting of the late promoter and tripartite leader sequence. Insertion in a nonessential E1 or E3 region of the viral genome will result in a viable virus capable of expressing HIFI in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a HIFI sequence. These signals include the ATG initiation codon and adjacent sequences. In cases where nucleic acid encoding HIFI, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express HIFI may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M. et al (1977) Cell 11:223–32) and adenine phosphoribosyltransferase (Lowy I. et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M. et al (1980) Proc Natl Acad Sci 77:3567–70); npt, which confers resistance to the aminoglycosides neomycin and G-418 (Colbere-Garapin F. et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C. A. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the HIFI polynucleotide sequence is inserted within a marker gene sequence, recombinant cells containing HIFI can be identified by the absence of marker gene function. Alternatively, a marker gene can be placed in tandem with a HIFI sequence under the control of a single promoter. Expression of the marker gene in response to induction or selection usually indicates expression of the tandem HIFI as well.

Alternatively, host cells which contain the coding sequence for HIFI and express HIFI may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding HIFI can be detected by DNA-DNA or DNA-RNA hybridization or amplification using probes, portions or fragments of HIFI-encoding nucleotides. Nucleic acid amplification based assays involve the use of oligonucleotides or oligomers based on the HIFI sequence to detect transformants containing HIFI DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of HIFI, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HIFI is preferred, but a competitive binding assay may be employed. These and other assays are described, among other places, in Hampton R. et al (1990, Serological Methods, a Laboratory Manual, APS Press, St Paul, Minn.) and Maddox D. E. et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to HIFI include oligolabeling, nick translation, end-labeling or PCR amplification using a labeled nucleotide. Alternatively, the HIFI sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway, N.J.), Promega (Madison, Wisc.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of HIFI

Host cells transformed with a HIFI-encoding nucleotide sequence may be cultured under conditions suitable for the expression and recovery of the encoded protein from cell culture. The protein produced by a recombinant cell may be contained intracellularly or secreted depending on the sequence and/or the vector used. As will be understood by those of skill in the art, expression vectors containing HIFI can be designed for efficient production and proper transmembrane insertion of HIFI into a prokaryotic or eukaryotic cell membrane. Other recombinant constructions may join HIFI to nucleotide sequence encoding a polypeptide domain which will facilitate purification of soluble proteins (Kroll D. J. et al (1993) DNA Cell Biol 12:441–53; cf discussion of vectors infra containing fusion proteins).

HIFI may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequences such as Factor XA or enterokinase (Invitrogen, San Diego, Calif.) between the purification domain and HIFI is useful to facilitate purification. One such expression vector provides for expression of a fusion protein compromising an HIFI and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying the HIFI from the fusion protein.

In addition to recombinant production, fragments of HIFI may be produced by direct peptide synthesis using solid-phase techniques (cf Stewart et al (1969) Solid-Phase Peptide Synthesis, W. H. Freeman Co, San Francisco; Merrifield J. (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Various fragments of HIFI may be chemically synthesized separately and combined using chemical methods to produce the full length molecule.

Uses of HIFI

The rationale for the use of polynucleotide and polypeptide sequences disclosed herein is based in part on the chemical and structural homology among the novel HIFI and the small hydrophobic IFI proteins from human and chimpanzee.

HIFI may be associated with diseases and conditions with which IFNs and possibly other cytokines are also associated. IFNS are produced in response to various cytokines and growth factors, in viral infections, inflammation, autoimmune diseases, and cancers. Accordingly, HIFI may be used in diagnosis and treatment of diseases such as, but not limited to, cancer (including renal, bladder and ovarian carcinomas, leukemias, and Kaposi's sarcoma), infections by viruses or other pathogens (such as HCV and leishmania), and conditions associated with inflammation or immune impairment such as rheumatoid and osteoarthritis and AIDS.

Furthermore, HIFI is useful as an investigative tool in the study of the control of gene expression by IFNs and other cytokines in both normal and diseased cells. HIFI or its fragments may be used to identify specific molecules with which it binds such as agonists, antagonists or inhibitors.

HIFI-specific antibodies are useful for the diagnosis of conditions and diseases associated with expression of the polypeptides. Antibodies specifically recognizing HIFI may be used to quantitate HIFI for diagnostic purposes.

The HIFI nucleic acid sequence of SEQ ID NO:2 can be incorporated into effective eukaryotic expression vectors and directly administered into somatic cells for gene therapy. In like manner, RNA transcripts produced in vitro may be encapsulated in and administered via liposomes. Such vectors and transcripts may function transiently or may be incorporated into the host chromosomal DNA for longer term expression.

In vivo delivery of genetic constructs into subjects is developed to the point of targeting specific cell types. The delivery to specific cells has been accomplished, for instance, by complexing nucleic acids with proteinous ligands that recognize cell specific receptors which mediate uptake (cf Wu G. Y. et al (1991) J Biol Chem 266:14338–42). Alternatively, recombinant nucleic acid constructs may be injected directly for local uptake and integration (Jiao S. et al (1992) Human Gene Therapy 3:21–33).

HIFI Antibodies

HIFI-specific antibodies are useful for the diagnosis and prognosis of conditions and diseases associated with expression of HIFI. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

HIFI for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of HIFI amino acids may be fused with those of another protein such as keyhole limpet hemocyanin and antibody produced against the chimeric molecule. Procedures well known in the art can be used for the production of antibodies to HIFI.

For the production of antibodies, various hosts including goats, rabbits, rats, mice, etc may be immunized by injection with HIFI or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to HIFI may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy,* Alan R. Liss Inc, New York. N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce HIFI-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G. and Milstein C. (1991; Nature 349:293–299).

Antibody fragments which contain specific binding sites for HIFI may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W. D. et al (1989) Science 256:1275–1281).

A variety of protocols for competitive binding or immunoradiometric assays using either polyclonal or monoclonal antibodies with established specificities are well known in the art. Such immunoassays typically involve the formation of complexes between HIFI and its specific antibody and the measurement of complex formation. A two-site, monoclonal-based immunoassay utilizing monoclonal antibodies reactive to two noninterfering epitopes on a specific HIFI protein is preferred, but a competitive binding assay may also be employed. These assays are described in Maddox D. E. et al (1983, J Exp Med 158:1211).

Diagnostic Assays using HIFI Specific Antibodies

Particular HIFI antibodies are useful for the diagnosis of conditions or diseases characterized by expression of HIFI or in assays to monitor patients being treated with HIFI, agonists or inhibitors. Diagnostic assays for HIFI include methods utilizing the antibody and a label to detect HIFI in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring HIFI, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HIFI is preferred, but a competitive binding assay may be employed. These assays are described, among other places, in Maddox, D. E. et al (1983, J Exp Med 158:1211).

In order to provide a basis for diagnosis, normal or standard values for HIFI expression must be established. This is accomplished by combining body fluids or cell extracts taken from normal subjects, either animal or human, with antibody to HIFI under conditions suitable for complex formation which are well known in the art. The amount of standard complex formation may be quantified by comparing various artificial membranes containing known quantities of HIFI with both control and disease samples from biopsied tissues. Then, standard values obtained from normal samples may be compared with values obtained from samples from subjects potentially affected by disease. Deviation between standard and subject values establishes the presence of disease state.

Drug Screening

HIFI, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between HIFI and the agent being tested, may be measured.

Another technique for drug screening which may be used for high throughput screening of compounds having suitable binding affinity to the HIFI is described in detail in "Determination of Amino Acid Sequence Antigenicity" by Geysen H. M., WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of HIFI and washed. Bound HIFI is then detected by methods well known in the art. Substantially purified HIFI can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HIFI specifically compete with a test compound for binding HIFI. In this manner, the antibodies can be used to detect the presence of any peptide which shares one or more antigenic determinants with HIFI.

Uses of the Polynucleotide Encoding HIFI

A polynucleotide encoding HIFI, or any part thereof, may be used for diagnostic and/or therapeutic purposes. For diagnostic purposes, the HIFI of this invention may be used to detect and quantitate gene expression in biopsied tissues in which expression of HIFI may be implicated. The diagnostic assay is useful to distinguish between absence, presence, and excess expression of HIFI and to monitor regulation of HIFI levels during therapeutic intervention. Included in the scope of the invention are oligonucleotide sequences, antisense RNA and DNA molecules, and PNAS.

Another aspect of the subject invention is to provide for hybridization or PCR probes which are capable of detecting polynucleotide sequences, including genomic sequences, encoding HIFI or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring HIFI, alleles or related sequences.

Probes may also be used for the detection of related sequences and should preferably contain at least 50% of the nucleotides from any of these HIFI encoding sequences. The hybridization probes of the subject invention may be derived from the nucleotide sequence of SEQ ID NO:2 or from genomic sequence including promoter, enhancer elements and introns of the naturally occurring HIFI. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

Other means for producing specific hybridization probes for HIFI DNAs include the cloning of nucleic acid sequences encoding HIFI or HIFI derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding HIFI may be used for the diagnosis of conditions or diseases with which the expression of HIFI is associated. For example, polynucleotide sequences encoding HIFI may be used in hybridization or PCR assays of fluids or tissues from biopsies to detect HIFI expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The HIFI nucleotide sequence disclosed herein provides the basis for assays that detect activation or induction associated with disease. The HIFI nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of HIFI nucleotide sequences in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for HIFI expression must be established. This is accomplished by combining body fluids or cell extracts taken from normal subjects, either animal or human, with HIFI, or a portion thereof, under conditions suitable for hybridization or amplification. Standard hybridization may be quantified by comparing the values obtained for normal subjects with a dilution series of HIFI run in the same experiment where a known amount of substantially purified HIFI is used. Standard values obtained from normal samples may be compared with values obtained from samples from patients afflicted with HIFI-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

Polymerase Chain Reaction (PCR) as described in U.S. Pat. Nos. 4,683,195 and 4,965,188 provides additional uses for oligonucleotides based upon the HIFI sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P. C. et al 1993 J Immunol Methods 159:235–44) or biotinylating (Duplaa C. et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to the genes encoding the small hydrophobic IFI proteins and its expression profile, the HIFI polynucleotide disclosed herein may provide the basis for the design of molecules for the treatment of cancer, pathogenic infections, inflammation or conditions associated with impaired immunity.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense HIFI. See, for example, the techniques described in Sambrook et al (supra) and Ausubel et al (supra).

The polynucleotides comprising full length CDNA sequence and/or its regulatory elements enable researchers to use HIFI as an investigative tool in sense (Youssoufian H. and H. F. Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding HIFI can be turned off by transfecting a cell or tissue with expression vectors which express high levels of a desired HIFI fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler L., personal communication) and even longer if appropriate replication elements are part of the vector system.

As mentioned above, modifications of gene expression can be obtained by designing antisense molecules, DNA, RNA or PNA, to the control regions of HIFI, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J. E. et al (In: Huber B. E. and B. I. Carr (1994) *Molecular and Immunologic Approaches*, Futura Publishing Co, Mt Kisco, N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of RNA encoding HIFI.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HIFI. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences for HIFI disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for HIFI can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C. M. (1993; Blood Rev 7:127–34) and Trask B. J. (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York, N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a HIFI on a physical chromosomal map and a specific disease (or predisposition to a specific disease) may help delimit the region of DNA associated withsequences of thesease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example, an STS based map of the human genome was recently published by the Whitehead-MIT Center for Genomic Research (Hudson T. J. et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22-23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Comnositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol;

starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of HIFI, such labeling would include amount, frequency and method of administration.

Theraceutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that HIFI may be used as a therapeutic agent to ameliorate the adverse effects of inflammatory cells in autoimmune diseases.

The examples below are provided to illustrate the subject invention and are not included for the purpose of limiting the invention.

EXAMPLES

I CDNA Library Construction

The KIDNNOT05 cDNA library was constructed from tissue removed from a female infant kidney with anoxia (lot #RU95-04-0274; International Institute of Advanced Medicine, Exton, Pa.). The frozen tissue was immediately homogenized and cells lysed with a Brinkmann Homogenizer Polytron PT-3000 (Brinkmann Instruments Inc., Westbury, N.Y.) in a guanidinium isothiocyanate solution.

Lysates were then loaded on a 5.7M CsCl cushion and ultracentrifuged in a SW28 swinging bucket rotor for 18 hours at 25,000 rpm at ambient temperature. The RNA was extracted once with acid phenol at pH 4.0 and precipitated with 0.3M sodium acetate and 2.5 volumes of ethanol, resuspended in DEPC-treated water and DNase treated for 25 min at 37° C. The reaction was stopped with an equal volume of pH 8.0 phenol, and the RNA was as above. The RNA was isolated using the Qiagen Oligotex kit (QIAGEN Inc, Chatsworth, Calif.) and used to construct the cDNA library.

The RNA was handled according to the recommended protocols in the SuperScript Plasmid System for cDNA Synthesis and Plasmid Cloning (catalog #18248-013; Gibco/ BRL). cDNAs were fractionated on a Sepharose CL4B column (catalog #275105, Pharmacia), and those cDNAs exceeding 400 bp were ligated into pSport I. The plasmid pSport I was subsequently transformed into DH5a™ competent cells (Cat. #18258-012, Gibco/BRL).

II Isolation and Sequencing of CDNA Clones

Plasmid DNA was released from the cells and purified using the Miniprep Kit (Catalogue # 77468; Advanced Genetic Technologies Corporation, Gaithersburg, Md.). This kit consists of a 96 well block with reagents for 960 purifications. The recommended protocol was employed except for the following changes: 1) the 96 wells were each filled with only 1 ml of sterile Terrific Broth (Catalog # 22711, LIFE TECHNOLOGIES™, Gaithersburg, Md.) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441f), using a Hamilton Micro Lab 2200 (Hamilton, Reno, Nev.) in combination with four Peltier Thermal Cyclers (PTC200 from M. J. Research, Watertown, Mass.) and Applied Biosystems 377 or 373 DNA Sequencing Systems (Perkin Elmer), and reading frame was determined.

III Homology Searching of CDNA Clones and Their Deduced Proteins

Each cDNA was compared to sequences in GenBank using a search algorithm developed by Applied Biosystems and incorporated into the INHERIT- 670 Sequence Analysis System. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul, S. F. et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques use BLAST (Altschul S. F. 1993 and 1990, supra) to search for identical or related molecules in nucleotide databases such as GenBank or the LIFESEQ™ database (Incyte, Palo Alto, Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of the search are reported as a list of libraries in which the full length sequence, or parts thereof, is represented, the abundance of the sequence, and the percent abundance. Abundance directly reflects the number of times a particular transcript is present in a cDNA library, and percent abundance is abundance divided by the total number of sequences examined in the library.

V Extension of HIFI to Full Length or to Recover Regulatory Elements

The nucleic acid sequence encoding full length HIFI (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known HIFI nucleotide sequence "outward" generating amplicons containing new, unknown nucleotide sequence for the region of interest. The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Mass.) and the following parameters:

| Step 1  | 94° C. for 1 min (initial denaturation)    |
|---------|--------------------------------------------|
| Step 2  | 65° C. for 1 min                           |
| Step 3  | 68° C. for 6 min                           |
| Step 4  | 94° C. for 15 sec                          |
| Step 5  | 65° C. for 1 min                           |
| Step 6  | 68° C. for 7 min                           |
| Step 7  | Repeat step 4–6 for 15 additional cycles   |
| Step 8  | 94° C. for 15 sec                          |
| Step 9  | 65° C. for 1 min                           |
| Step 10 | 68° C. for 7:15 min                        |
| Step 11 | Repeat step 8–10 for 12 cycles             |
| Step 12 | 72° C. for 8 min                           |
| Step 13 | 4° C. (and holding)                        |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent $E.\ coli$ cells (in 40 μl of appropriate media) are transformed with 3 μl of ligation mixture and cultured in 80 μl of SOC medium (Sambrook J. et al, supra). After incubation for one hour at 37° C., the whole transformation mixture is plated on Luria Bertani (LB)-agar (Sambrook J. et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTh DNA polymerase, a vector primer and one or both of the gene specific primers used for the extension reaction are added to each well. Amplification is performed using the following conditions:

| Step 1 | 94° C. for 60 sec                            |
|--------|----------------------------------------------|
| Step 2 | 94° C. for 20 sec                            |
| Step 3 | 55° C. for 30 sec                            |
| Step 4 | 72° C. for 90 sec                            |
| Step 5 | Repeat steps 2–4 for an additional 29 cycles |
| Step 6 | 72° C. for 180 sec                           |
| Step 7 | 4° C. (and holding)                          |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [γ-$^{32}$P] adenosine triphosphate (Amersham, Chicago, Ill.) and T4 polynucleotide kinase (DuPont NEN®, Boston, Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba I, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

The nucleotide sequence encoding HIFI, or any part thereof, is used to inhibit in vivo or in vitro expression of naturally occurring HIFI. Although use of antisense oligonucleotides, comprising about 20 base-pairs, is specifically described, essentially the same procedure is used with larger cDNA fragments. An oligonucleotide based on the coding sequence of HIFI as shown in FIG. 1 is used to inhibit expression of naturally occurring HIFI. The complementary oligonucleotide is designed from the most unique 5' sequence as shown in FIG. 1 and used either to inhibit transcription by preventing promoter binding to the upstream nontranslated sequence or translation of an HIFI transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIG. 1.

VIII Expression of HIFI

Expression of HIFI is accomplished by subcloning the cDNAs into appropriate vectors and transfecting the vectors into host cells. In this case, the cloning vector, pSport, previously used for the generation of the cDNA library is used to express HIFI in $E.\ coli$. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length HIFI. The signal sequence directs the secretion of HIFI into the bacterial growth media which can be used directly in the following assay.

IX HIFI Activity

The binding of HIFI to a receptor molecule is assayed by monitoring the resulting changes in enthalpy (heat production or absorption) in an isothermal titration microcalorimeter (Micro-Cal Inc. Northampton, Mass.). Titration microcalorimetry measurements do not require labeling of the ligand or receptor molecules; detection is based solely on the intrinsic change in the heat of enthalpy upon binding. Multiple computer-controlled injections of a known volume of HIFI in solution are directed into a thermally-controlled chamber containing the receptor. The change in enthalpy after each injection is plotted against the number of injections, producing a binding isotherm. The volumes and concentrations of the injected HIFI and of the receptor are used along with the binding isotherm to calculate values for the number, affinity, and association of HIFI with the candidate receptor.

X Production of HIFI Specific Antibodies

HIFI substantially purified using PAGE electrophoresis (Sambrook, supra) is used to immunize rabbits and to produce antibodies using standard protocols. The amino acid sequence translated from HIFI is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIG. 3) is described by Ausubel F. M. et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F. M. et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HIFI Using Specific Antibodies

Naturally occurring or recombinant HIFI is substantially purified by immunoaffinity chromatography using antibodies specific for HIFI. An immunoaffinity column is constructed by covalently coupling HIFI antibody to an activated chromatographic resin such as CnBr-activated Sepharose (Pharmacia Biotech). After the coupling, the resin is blocked and washed according to the manufacturer's instructions.

Cellular fractions from cells containing HIFI are prepared by solubilization of the whole cell and isolation of subcellular fractions by differential centrifugation, by the addition of detergent, or by other methods well known in the art. Alternatively, soluble HIFI containing a signal sequence may be secreted in useful quantity into the medium in which the cells are grown.

A fractionated HIFI-containing preparation is passed over the immunoaffinity column, and the column is washed under conditions that allow the preferential absorbance of HIFI (eg. high ionic strength buffers in the presence of detergent). The column is eluted under conditions that disrupt antibody/HIFI binding (eg. a buffer of pH 2–3 or a high concentration of a chaotrope such as urea or thiocyanate ion), and HIFI is collected.

XII Identification of Molecules Which Interact with HIFI

HIFI is useful as a research tools for identification, characterization and purification of molecules with which it interacts. In one embodiment of affinity purification, HIFI is covalently coupled to a chromatography column. Cells and their membranes are extracted, endogenous HIFI is removed and various HIFI-free subcomponents are passed over the column. HIFI-associated molecules bind to the column by virtue of their biological affinity. The HIFI-complex is recovered from the column, dissociated and the recovered molecule is subjected to N-terminal protein sequencing, nucleic acid sequencing, or high-performance liquid chromatography/mass spectrometry (HPLC/MS), depending on the type of molecule. The amino acid or nucleotide sequence or mass spectral analysis is then used to identify the captured molecule or, in the case of a protein ligand, to design degenerate oligonucleotide probes for cloning iprobes for cloning its gene from an appropriate cDNA library.

In an alternate method, monoclonal antibodies are raised against HIFI and screened to identify those compounds which inhibit the binding of the antibody to HIFI. These monoclonal antibodies may then used in affinity purification or expression cloning of associated molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated or substantially purified hydrophobic interferon inducible protein comprising the amino acid sequence of SEQ ID NO: 1.

2. An isolated or substantially purified polynucleotide sequence encoding the hydrophobic interferon inducible protein of claim 1.

3. An isolated or substantially purified polynucleotide sequence comprising the nucleic acid of SEQ ID NO:2.

4. An isolated or substantially purified polynucleotide sequence which is complementary to SEQ ID NO:2.

5. A recombinant expression vector containing the polynucleotide sequence of claim 3.

6. A recombinant host cell containing the expression vector of claim 5.

7. A method for producing a hydrophobic interferon inducible protein having SEQ ID NO:1 comprising the steps of:

a) culturing the host cell of claim 6 under conditions suitable for the expression of the polypeptide; and b) recovering the polypeptide from the host cell culture.

8. A composition comprising a hydrophobic interferon inducible protein having SEQ ID NO:1 and a pharmaceutically acceptable excipient.

* * * * *